United States Patent [19]

Suyama

[11] Patent Number: 4,944,296
[45] Date of Patent: Jul. 31, 1990

[54] ELECTRONIC TOOTHBRUSH

[76] Inventor: Hideo Suyama, 65, Higashi-Juban, Sendai-Shi, Miyahi, Japan

[21] Appl. No.: 230,752

[22] Filed: Aug. 10, 1988

[30] Foreign Application Priority Data

Aug. 10, 1987 [JP] Japan .................................. 62-198119
Jan. 5, 1988 [JP] Japan ...................................... 63-519

[51] Int. Cl.$^5$ ............................................... A61N 1/30
[52] U.S. Cl. .................................... 128/393; 15/167.1; 128/24.5; 604/20
[58] Field of Search ..................... 128/393, 62 A, 24.1, 128/24.5; 15/167.1, 167.2, 110; 604/20; 310/317

[56] References Cited

U.S. PATENT DOCUMENTS

| | | | |
|---|---|---|---|
| 3,488,788 | 1/1970 | Robinson | 128/62 A |
| 4,192,035 | 3/1980 | Kuris | 128/62 A |
| 4,236,510 | 12/1980 | Hatter et al. | 128/62 A |
| 4,502,497 | 3/1985 | Siahou | 604/20 |
| 4,691,718 | 9/1987 | Sakuma et al. | 128/393 |
| 4,726,806 | 2/1988 | Hukuba | 15/167.1 |

FOREIGN PATENT DOCUMENTS

| | | | |
|---|---|---|---|
| 0027390 | 8/1973 | Japan | 15/167.1 |
| 405601 | 6/1933 | United Kingdom | 128/393 |
| 2135193 | 8/1984 | United Kingdom | 15/167.1 |

OTHER PUBLICATIONS

Technical Paper, Piezo Film Sensing Devices by William B. Powers, Society of Manufacturing Engineers Conference, Nov. 11–13, 1986.

Primary Examiner—Edward M. Coven
Assistant Examiner—Jessica J. Harrison
Attorney, Agent, or Firm—Wenderoth, Lind & Ponack

[57] ABSTRACT

An electronic toothbrush has a piezo-electric element with electrodes on both sides mounted in a handle of a toothbrush. Electrons generated due to vibration of a handle effectively remove dental plaque having a tendency to be charged with positive electricity. A diode is electricity connected to electrodes on both sides of the piezo-electric element to rectify the electric current to neutralize positive and negative charges generated on both electrodes when positive charges are generated on an electrode in close vicinity to a brushing portion of a handle.

6 Claims, 4 Drawing Sheets

ELECTRONIC TOOTHBRUSH

BACKGROUND OF THE INVENTION

This invention relates to an electronic toothbrush for the purpose of removing dental plaque by means of brushing and discharging electrons.

Tooth decay is a disease wherein hard inorganic teeth are decayed by an acid produced by bacteria in a mouth. Dental plaque, that is composed of propagating bacteria, depositing protein and inorganic compounds in saliva, overspreads and build up on a tooth-surface. Tartar is produced by calcification of the plaque its main ingredient is calcium phosphate. Pyorrhea alveala-ris is an inflammation of gums caused by plaque left on a root of a tooth and under a gum line.

A conventional electronic toothbrush using a dry battery or solar battery generates electrons that decompose plaque and the neutralize latic acid by means of a reducing process around teeth. This reducing process is caused of the electrons that flow through conductive saliva and water with positive and negative ions, for example, kalium, sodium, magnesium, bicarbonate, chlorine, phosphoric acid, etc. However, the conventional electronic toothbrush is generally high in price because of using a complicated waterproof structure and an expensive battery. Furthermore, there are other drawbacks in that a life of a dry battery is limited and an output voltage of a solar battery is low.

SUMMARY OF THE INVENTION

It is an object of the present invention, therefore, to simplify a structure of an electronic toothbrush, and to reduce costs without using a high price battery, and to obtain a high output voltage and to get unlimited life. These objects of the present invention are realized by utilizing a piezo-electric element mounted in a handle of a toothbrush.

Electrodes are formed on both sides of said piezo-electric element located in the center portion of the handle, and then the electrode on one side is exposed in close vicinity to the brushing portion and the electrode on the other side is exposed on the gripped portion of the handle. On the occasion of toothbrushing, positive and negative charges are generated on both sides of the piezo-electric element as a result of bending and vibration of the handle.

It is necessary to select proper polarity of the piezo-electric element and put in a diode between both electrodes for generating selectively negative charges on the electrode exposed in close vicinity to the brushing portion. Electrons flow from the electrode near the brushing portion to the electrode on the gripped portion of the handle, through saliva and water in a mouth, teeth, a root of tooth, a human body and a hand. Consequently, dental plaque is removed effectively by a reducing process due to the electrons around the teeth.

BRIEF DESCRIPTION OF THE DRAWINGS

The present invention is described in greater detail with reference to the drawings, in which.

DESCRIPTION OF THE PREFERRED EMBODIMENTS

Figure 1:
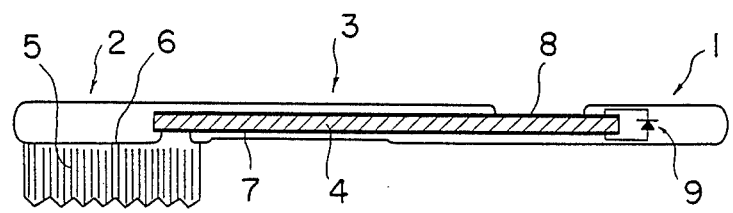
FIG. 1 is a cross sectional view of a basic embodiment of the present invention.

The basic embodiment of the present invention is shown is the cross sectional view of FIG. 1. A piezo-electric element 4 with a piezo-electric characteristic is operatively mounted in a handle 3 of a toothbrush between a gripped portion 1 and a brushing portion 2 of the handle 3. A diode 9 with a rectifying action is used to electrically connect an electrode 7 and an electrode 8 formed on both sides of the piezo-electric element 4. The electrode 7 is exposed in close vicinity to the brushing portion 2 on the brush 5 side of the handle 3, and the electrode 8 is exposed on the opposite side. The brush 5 is laid on the surface 6 of the brushing portion 2.

Figure 2:
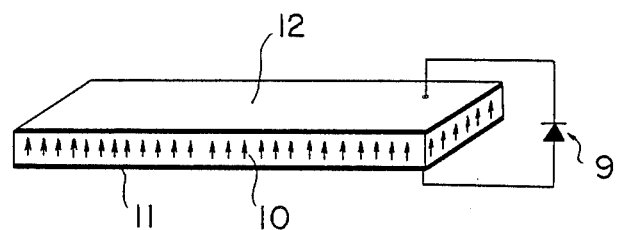
FIG. 2 is illustrative of a principle piezo-electric element used in the present invention.

FIG. 2 illustrates the principle of generating the output voltage in the piezo-electric element 10. When the piezo-electric element 10 is expanded and contracted horizontally, positive and negative charges are generated on the eletrodes 11 and 12, respectively. The piezo-electric element 10, for example, a polyvinylidene fluoride film, consists of countless dipoles that allow the element to create electric charges resulting from expansion and contraction applied to the element. If both electrodes 11 and 12 are electrically connected, the electric current flows from the electrode with negative charges to the electrode with positive charges.

Figure 3:
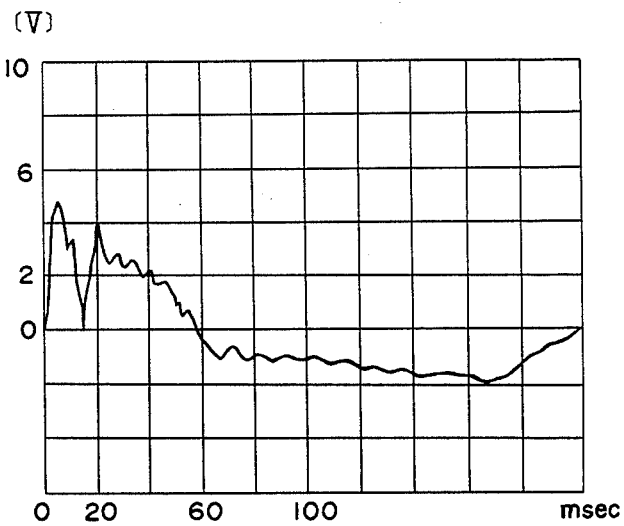
FIGS. 3 and 4 are characteristic curves observed in an oscilloscope of output voltages generated by piezoelectric elements without and with a diode, respectively.
Figure 4:
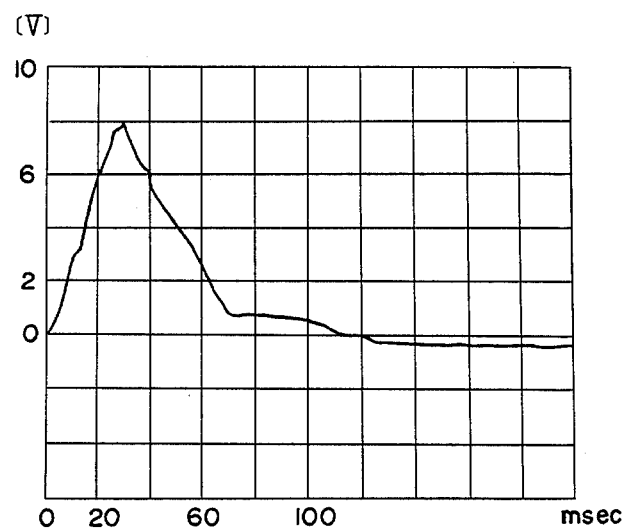

FIGS. 3 and 4 illustrate the characteristic curves of the output voltage generated from the piezo-electric element, as shown in FIG. 2, mounted on a piece of plastic plate as a cantilever at the time of tapping without and with the diode 9, respectively. The ordinate axis denotes the voltage V by 2 volt per one scale and the abscissas axis the time t by 20 msec per one scale, respectively. In the characteristic curve of FIG. 3, without the diode 9, the output voltage is lower and the output voltage of opposite polarity is generated at the time of resilience of the plastic plate with the piezo-electric element. In FIG. 4, with the diode 9, the output voltage is higher and nearly rectified without opposite polarity.

The present invention utilizes the phenomenon mentioned above. When the handle 3 of the toothbrush shown in FIG. 1 is bent, the output voltage is generated according to expansion and contraction of the piezo-electric element 4. In other words, the output voltage results in between the brush 5 side electrode 7 exposed in close vicinity to the brushing portion 2 and the other electrode 8 exposed on the gripped portion 1 of the handle 3. The external force is always applied to the brush 5 when tooth-brushing, and therefore the handle 3 of the toothbrush is bent almost always toward the surface 6 with the brush 5. The piezo-electric element 4 is polarized so that the negative charges are generated on the electrode 7 due to the expansion and the contraction corresponding to the bending of the handle 3. Electrons flow in the circuit from the electrode 7 with negative charges to the electrode 8 with positive charges, through conductive salvia and water in a mouth, teeth or gums, a human body and a hand. Furthermore, to generate the electrons only out from the electrode 7 and to obtain a higher output voltage, the diode 9 rectifying action is electrically connected between the electrodes 7 and 8. On the occasion that positive and negative charges are generated on the electrodes 7 and 8, respectively, most of the electric current flows in the diode 9 with low resistivity due to the forward direction, not in the circuit of the mouth and the human body with relatively high resistivity. Then, the electric current from the electrode 7 to the electrode 8 is rectified as shown in FIG. 4, the higher negative output voltages is generated only on the electrode 7. In general, the diode used in the present invention is low priced due to the small size and has a water-resisting quality compared with a dry battery. Moreover, the piezo-electric element, a polyvinylidene fluoride film, for example, is low priced and water-resistant.

The other embodiments of the present invention are illustrated in FIGS. 5-10.

Figure 5:
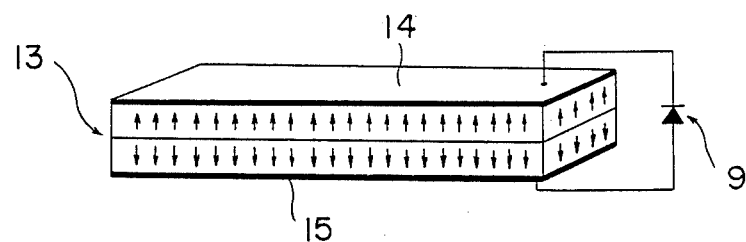
FIGS. 5 and 6 are perspective views illustrative of piezo-electric bimorphs.

The bending motion of the plastic handle 3 between the gripped portion 1 and the brushing portion 2 is mentioned above in FIG. 1. The negative charges corresponding to the bending of the handle 3 must be generated on the electrode 7. As mentioned in the summary of the invention, it is necessary to obtain electrons near the brushing portion 2 for the purpose of effective removal of plaque and tartar by brushing and a reducing process. A piezo-electric bimorph 13, a laminate of the piezo-electric elements as shown in FIG. 5, generates different charges on the electrodes 14 and 15 in response to the bending.

Figure 6:
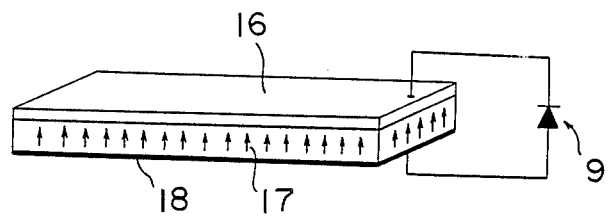
Figure 7:
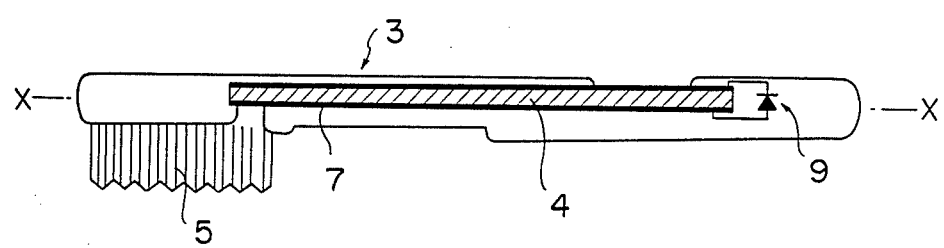
FIGS. 7 and 8 are cross sectional views illustrative of location of piezo-electric elements in handles.
Figure 8:
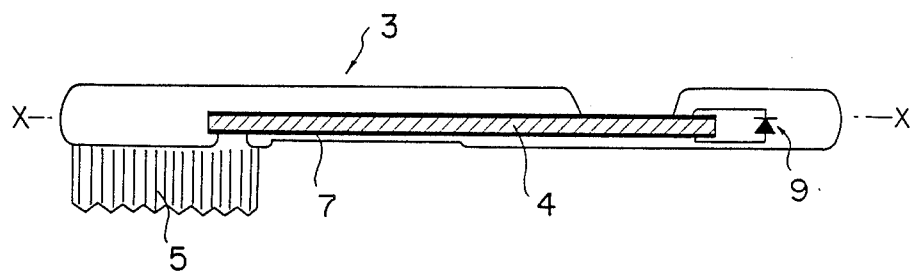

Another piezo-electric bimorph, as shown in FIG. 6, which is a laminate of a piezo-electric element 17 and a metal sheet 16, can be used in the present invention. In this case, different charges are generated on electrode 18 and the metal sheet 16 due to the bending. The piezo-electric element 17, a polyvinyliden fluoride film, is relatively flexible, but the metal sheet 16 is rigid and has little flexibility of expansion and contraction. On the occasion that the piezo-electric element 17 of the bimorph in FIG. 6 is located on the brush side of the handle of the toothbrush, the piezo-electric element 17 is mainly expanded. In the contrary case, the piezo-electric element 17 is mostly contracted when brushing teeth. The piezo-electric elements of the bimorphs shown in FIGS. 5 and 6 must be polarized so that the negative charges are generated on the electrodes near the brushing portion. Subsequently, the other embodiments shown in FIGS. 7 and 8 which can achieve effectively the object of the present invention use the single layer piezo-electric elements 4, not bimorphs. These single layer elements 4 that are mounted in the location shifted from the center line X—X of the handle 3 are cousequently contracted and expanded as shown in FIGS. 7 and 8, respectively, when bending of the handle 3. The polarizing directions of the piezo-electric elements 4 are perpendicular to the elements 4, and opposite directions, in FIGS. 7 and 8, respectively. As noted above, the object of the present invention is achieved according to locating the piezo-electric elements 4 which are expanded and contracted due to the bending of the handle 3. It is a matter of course that the diodes 9 having a rectifying action are electricaly connected to both opposite electrodes to gain effectively the higher output voltage.

Figure 9:
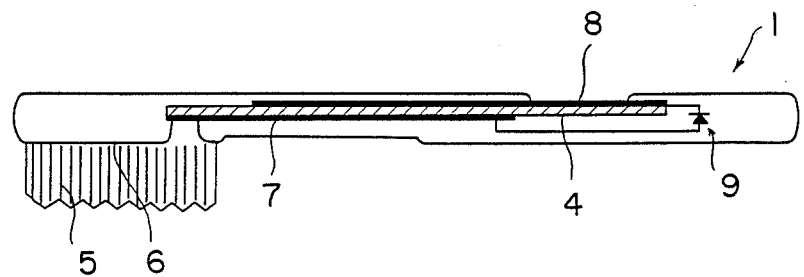
FIG. 9 is a cross sectional view illustrative of a reformed embodiment of the present invention.

In the embodiment of the present invention, as shown in FIG. 9, the only electrode 7 formed on one side of the piezo-electric element 4 is exposed in close vicinity to the surface 6 of the brushing portion, and the only electrode 8 is exposed on the gripped portion 1, respectively. Moreover, the part of the piezo-electric element 4 with electrodes on both sides is sealed hermetically in the plastic of the handle, hence the short circuit between electrodes 7 and 8 is not caused when toothbrushing.

Figure 10:
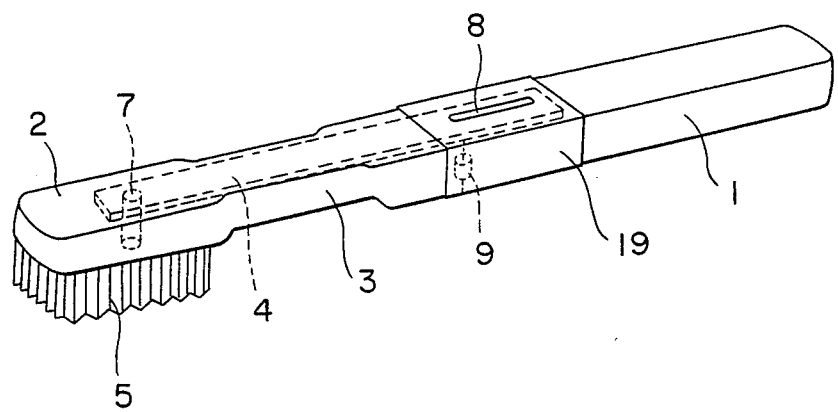
FIG. 10 is a perspective view illustrative of another embodiment of the present invention.

The more practical embodiment of the present invention is illustrated in FIG. 10. A metal plate 19 is connected directly and operatively to the electrode 8 exposed on the gripped portion 1 of the handle 3 and fastened around the gripped portion 1. Furthermore, the diode 9 mounted in the gripped portion 1 is electrically connected between the electrode 7 and the metal plate 19. When brushing teeth, a hand almost always touches the metal plate 19, and therefore the object of the present invention is effectively achieved.

What is claimed is:

1. An electronic toothbrush comprising: a piezo-electric element with piezo-electric characteristic mounted in a handle between a gripped portion and a brushing portion of said electronic toothbrush for producing an electrical potential upon deformation due to use of the toothbrush by a user; an exposed electrode disposed in close vicinity to said brushing portion and an opposite exposed electrode disposed on said gripped portion of said handle formed on both sides of said piezo-electric element, said electrodes disposed such that said exposed electrode is in electrical contact with mouth of user during use of toothbrush by user and said opposite exposed electrode is in electrical contact with hand of user during use of toothbrush by user; and a diode with a rectifying action electrically connected to said electrodes formed on both sides of said piezo-electric element so as to cause an essentially unidirectional potential to be produced by said piezo-electric element.

2. An electronic toothbrush as claimed in claim 1, wherein said piezo-electric element is composed of a thin and flexible piezo-electric material.

3. An electronic toothbrush as claimed in claim 1, wherein said piezo-electric element is composed of a bimorph structure.

4. An electronic toothbrush comprising: a piezo-electric element with piezo-electric characteristic mounted in a handle between a gripped portion and a brushing portion of said electronic toothbrush for producing an electrical potential upon deformation due to use of the toothbrush by a user; an exposed electrode disposed in close vicinity to said brushing portion and an opposite exposed electrode disposed on said gripped portion of said handle formed on both sides of said piezo-electric element, said electrodes disposed such that said exposed electrode is in electrical contact with mouth of user during use of toothbrush by user and said opposite exposed electrode is in electrical contact with hand of user during use of toothbrush by user; wherein said handle is composed of a plastic material having compartments for covering upper and lower portions of said piezo-electric element formed such that thicknesses of said plastic compartments for covering said piezo-electric element are different at upper and lower portions of said piezo-electric element.

5. An electronic toothbrush as claimed in claim 4, wherein said piezo-electric element is composed of a thin and flexible piezo-electric material.

6. An electronic toothbrush comprising: a piezo-electric element with piezo-electric characteristic mounted in a handle between a gripped portion and a brushing portion of said electronic toothbrush for producing an electrical potential upon deformation due to use of the toothbrush by a user; an exposed electrode disposed in close vicinity to said brushing portion and an opposite exposed electrode disposed on said gripped portion of said handle formed on both sides of said piezo-electric element, said electrodes disposed such that said exposed electrode is in electrical contact with mouth of user during use of toothbrush by user and said opposite exposed electrode is in electrical contact with hand of user during use of toothbrush by user; and a metal plate electrically connected to said opposite exposed electrode and a diode, said diode being electrically connected between said exposed electrode and said opposite exposed electrode of said piezo-electric element, and said metal plate being disposed around said gripped portion of said handle.

* * * * *